United States Patent [19]

Okada et al.

[11] Patent Number: 5,085,851

[45] Date of Patent: Feb. 4, 1992

[54] DENTAL PLAQUE-DEGRADING COMPOSITIONS

[75] Inventors: Gentaro Okada, Shizuoka; Hirofumi Akano, Handa; Takeshi Sato, Handa; Hajime Okumura, Handa; Kawamura, Kounan, all of Japan

[73] Assignee: Nakano Vinegar Co., Ltd., Handa, Japan

[21] Appl. No.: 552,533

[22] Filed: Jul. 16, 1990

[30] Foreign Application Priority Data

Jul. 29, 1989 [JP] Japan ................... 1-195424

[51] Int. Cl.$^5$ .................. A61K 7/16; A61K 7/28; A61K 9/68
[52] U.S. Cl. ........................ 424/50; 514/900; 514/901; 514/902; 424/48
[58] Field of Search ............. 424/50; 514/900, 901, 514/902

[56] References Cited

U.S. PATENT DOCUMENTS

| | | | |
|---|---|---|---|
| 3,686,393 | 8/1972 | Woodruff et al. | 424/50 |
| 4,082,841 | 4/1978 | Pader | 424/50 |
| 4,152,418 | 5/1979 | Pader | 424/50 |
| 4,154,815 | 5/1979 | Pader | 424/50 |
| 4,469,673 | 9/1984 | Iioka et al. | 424/50 |
| 4,576,816 | 3/1986 | Suganuma et al. | 424/50 |

FOREIGN PATENT DOCUMENTS

| | | | |
|---|---|---|---|
| 755331 | 10/1970 | Belgium | 424/50 |
| 756289 | 3/1971 | Belgium | 424/50 |
| 1467951 | 2/1969 | Fed. Rep. of Germany | 424/50 |
| 4675M | 1/1967 | France | 424/50 |
| 1270200 | 4/1972 | United Kingdom | 424/50 |
| 1284728 | 8/1972 | United Kingdom | 424/50 |

*Primary Examiner*—Shep K. Rose
*Attorney, Agent, or Firm*—Sherman and Shalloway

[57] ABSTRACT

A dental plaque-degrading composition containing endodextranase produced by *Arthrobacter globiformis* W31 exhibiting high degradation efficacy to insoluble glucan produced by *Streptococcus mutans* IFO 13955, the dental plaque-degrading composition additionally containing α-amylase of various origins. These compositions are useful for preventing the settlement of *Streptococcus mutans* in the oral cavity and the formation of new dental plaque and for preventing the dental caries, and provided in the form of dentifrices, denture detergents, troches, mouth washes, chewing gums or candies.

7 Claims, 4 Drawing Sheets

— ○ — : Arthrobacter globiformis W31 ENDODEXTRANASE (1.0 UNIT)
--- ○ --- : Arthrobacter globiformis W31 ENDODEXTRANASE (0.3 UNIT)
— ■ — : BARLEY MALT α-AMYLASE (1.0 UNIT)
— ● — : Bacillus sp. α-AMYLASE (1.0 UNIT)
— ▲ — : Bacillus licheniformis α-AMYLASE (1.0 UNIT)

FIG.3

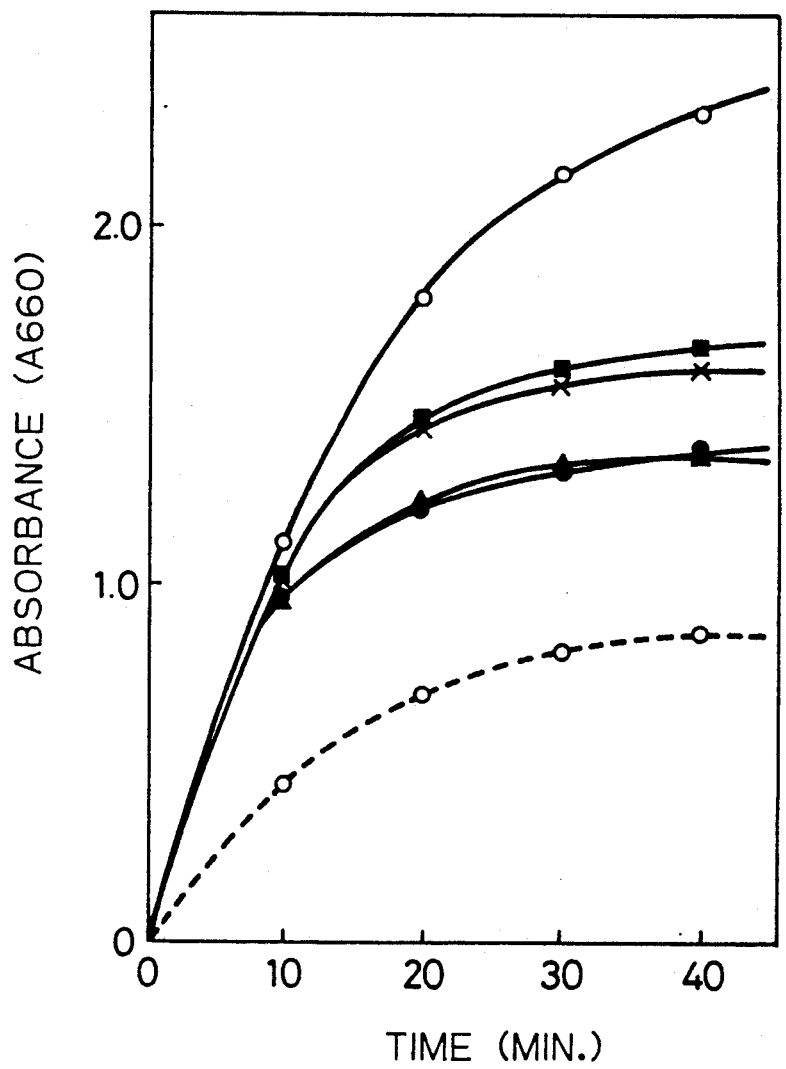

———○——— : Arthrobacter globiformis W31 ENDODEXTRANASE (1.0 UNIT)
- - -○- - - : Arthrobacter globiformis W31 ENDODEXTRANASE (0.3 UNIT)
———■——— : Arthrobacter globiformis W31 ENDODEXTRANASE (0.3 UNIT)
　　　　　　+BARLEY MALT α—AMYLASE (0.7 UNIT)
———×——— : Arthrobacter globiformis W31 ENDODEXTRANASE (0.3 UNIT)
　　　　　　+HUMAN SALIVARY α—AMYLASE (0.7 UNIT)
———●——— : Arthrobacter globiformis W31 ENDODEXTRANASE (0.3 UNIT)
　　　　　　+Bacillus sp. α—AMYLASE (0.7 UNIT)
———▲——— : Arthrobacter globiformis W31 ENDODEXTRANASE (0.3 UNIT)
　　　　　　+Bacillus licheniformis α—AMYLASE (0.7 UNIT)

FIG. 4

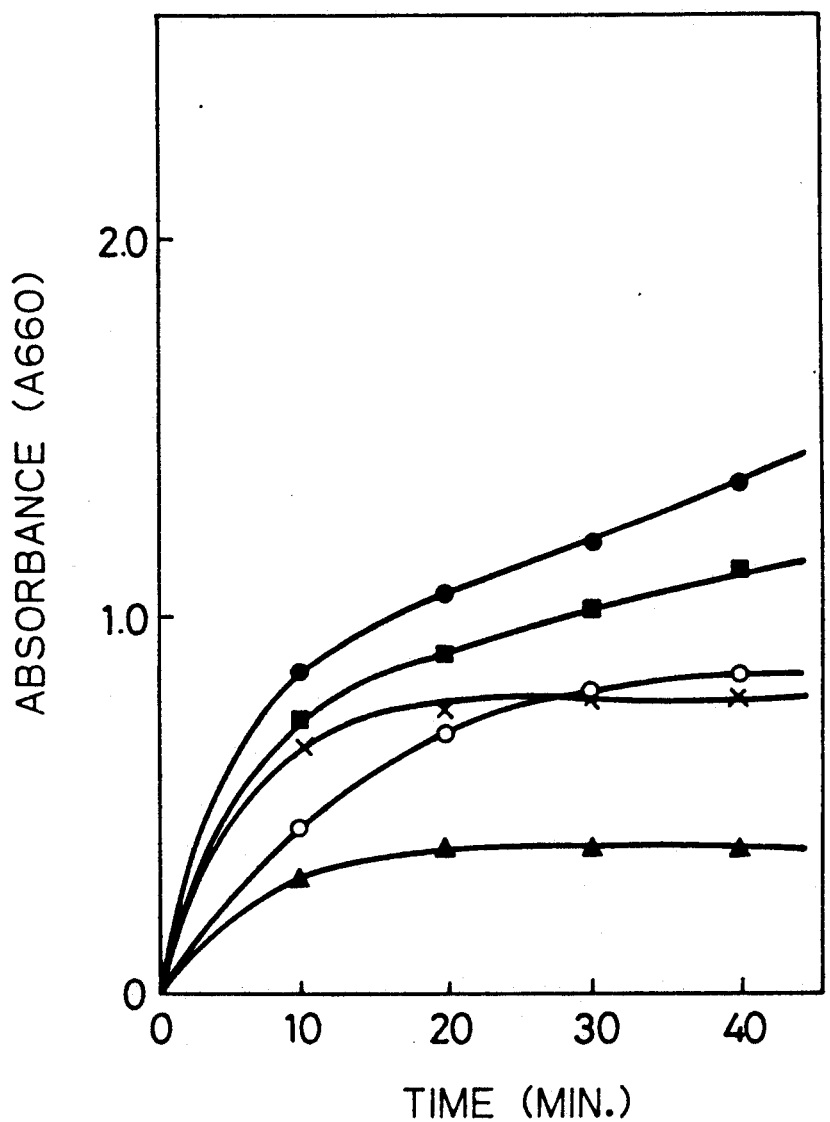

—○— : Arthrobacter globiformis W31 ENDODEXTRANASE (0.3 UNIT)
—●— : Arthrobacter globiformis W31 ENDODEXTRANASE (0.3 UNIT)
       +Bacillus licheniformis α-AMYLASE (0.7 UNIT)
—■— : Arthrobacter globiformis W31 ENDODEXTRANASE (0.2 UNIT)
       +Bacillus licheniformis α-AMYLASE (0.8 UNIT)
—×— : Arthrobacter globiformis W31 ENDODEXTRANASE (0.1 UNIT)
       +Bacillus licheniformis α-AMYLASE (0.9 UNIT)
—▲— : Bacillus licheniformis α-AMYLASE (1.0 UNIT)

DENTAL PLAQUE-DEGRADING COMPOSITIONS

This invention relates to a dental plaque-degrading composition which degrades insoluble glucan (mutan), principal constituent of dental plaque, produced by cariogenic *Streptococcus mutans* highly efficiently, and which prevents the formation of new dental plaque. The inventive composition serves to prevent the settlement of *Streptococcus mutans* in the oral cavity, thus preventing dental caries.

BACKGROUND OF THE INVENTION

It is believed that dental plaque formed and adhered to the surface of teeth consists of 70% intraoral bacteria, approx. 20% polysaccharides synthesized by the bacteria and approx. 10% food debris. The intraoral bacterium *Streptococcus mutans* has been regarded as being cariogenic bacterium. *Streptococcus mutans* produces glucosyltransferase and dextran synthetase, these enzymes produce cohesive glucan which is principal component of dental plaque, for example, mutan, dextran or the like, from sucrose. In addition, acids produced and accumulated inside the dental plaque by this bacterium demineralize the enamel of teeth to induce dental caries. That is, the dental plaque is considered a causative of caries.

PRIOR ART

In order to clean teeth, mechanical removal food debris and dental plaque adhered to the surface of teeth using a tooth brush mainly in combination with dentifrice has hitherto been adopted. However, if a tooth brush is used in an inappropriate manner, interdental space, occlusal surfaces of molar teeth, etc. cannot be cleaned thoroughly. This fact leads to the formation of intraoral diseases such as dental caries, alveolar pyorrhea, gingivitis, etc. In order to remove these disadvantages of brush cleaning, it has been proposed to remove dental plaque biochemically by incorporating dextranase into intraoral compositions such as a dentifrice (Japanese Patent Publication No. 34897/1973).

As dextranase-producing bacteria, many microorganisms have been known, for example, filamentous fungi belonging to the genera Asperqillus, Penicillium, Fusarium, Chaetomium, Humicola, etc.; actinomycetes belonging to the genera Actinomyces, Streptomyces, etc. and bacteria belonging to the genera Bacillus, Brevibacterium, Corynebacterium, Cellvibrio, Lactobacillus, etc.

PROBLEMS TO BE SOLVED BY THE INVENTION

However, none of dextranase produced by the above microorganisms has satisfactory dental plaque-degrading activity. Therefore, there is a need for dextranase having high dental plaque-degrading activity in the field of the art.

Dextranase has hitherto been produced by culturing a dextranase-producing microorganism by adding bacterial dextran as a carbon source and at the same time as an inducer.

Dextran, however, is expensive, so that the production cost of dextranase becomes high. From this point of view, there is also a need for a means for increasing the activity of dextranase and degrading dental plaque still effectively even in the case of using a small amount of dextranase.

SUMMARY OF THE INVENTION

The object of the present invention is to provide a dental plaque-degrading composition containing novel endodextranase having high dental plaque-degrading activity and particularly, to provide a dental plaque-degrading composition containing a component which synergistically potentiates the action of endodextranase and thereby degrades insoluble glucan in dental plaque and dental plaque itself efficiently, thus inhibiting the deposit of new dental plaque effectively to prevent the formation of new dental caries.

Endodextranase (scientific name: 1,6-α-D-glucan-6-glucanohydrolase, EC 3.2.1.11) is known as an endohydrolase for bacterial dextran, and can specifically cleave α-1,6-glucosidic linkage of insoluble glucan (mutan) produced by cariogenic *Streptococcus mutans* and the like. As will be shown in Examples hereinbelow, the endodextranase from the genus Arthrobacter exhibits 3-6 times more enzymatic activity than those derived from microorganisms belonging to the genera Chaetomium or Penicillium in degrading insoluble glucan produced by *Streptococcus mutans* IFO 13955, even if used in enzymatically equivalent amount (see Example 2). Furthermore, it has been found that combined use of α-amylase with endodextranase leads to a marked synergistic effect upon the degradation of the aforementioned insoluble glucan (see Examples 4 and 5).

Aforementioned use of α-amylase also provides an advantage of reducing the amount of expensive endodextranase to be used.

Endodextranase used in the present invention also contributes to the degradation of insoluble glucan in dental plaque synergistically in the presence of human salivary α-amylase. Also $Ca^{2+}$ in saliva acts as an effective protective agent for endodextranase used in the present invention.

Accordingly, the effect of the present dental plaque-degrading composition becomes very marked, allowing effective prevention of the settlement of *Streptococcus mutans* in the oral cavity, the formation of new dental plaque and also the formation of dental caries.

BRIEF EXPLANATION OF THE DRAWINGS

FIG. 3 shows the comparison of insoluble glucan-degrading activity between the single use of the endodextranase from *Arthrobacter globiformis* W31 and the combined use thereof with various α-amylases of different origins.

FIG. 4 shows the comparison of insoluble glucan-degrading activity between the single use of the endodextranase from *Arthrobacter globiformis* W31 and the combined use thereof with various amounts of α-amylase from *Bacillus licheniformis*.

DESCRIPTION OF THE INVENTION

Figure 1:
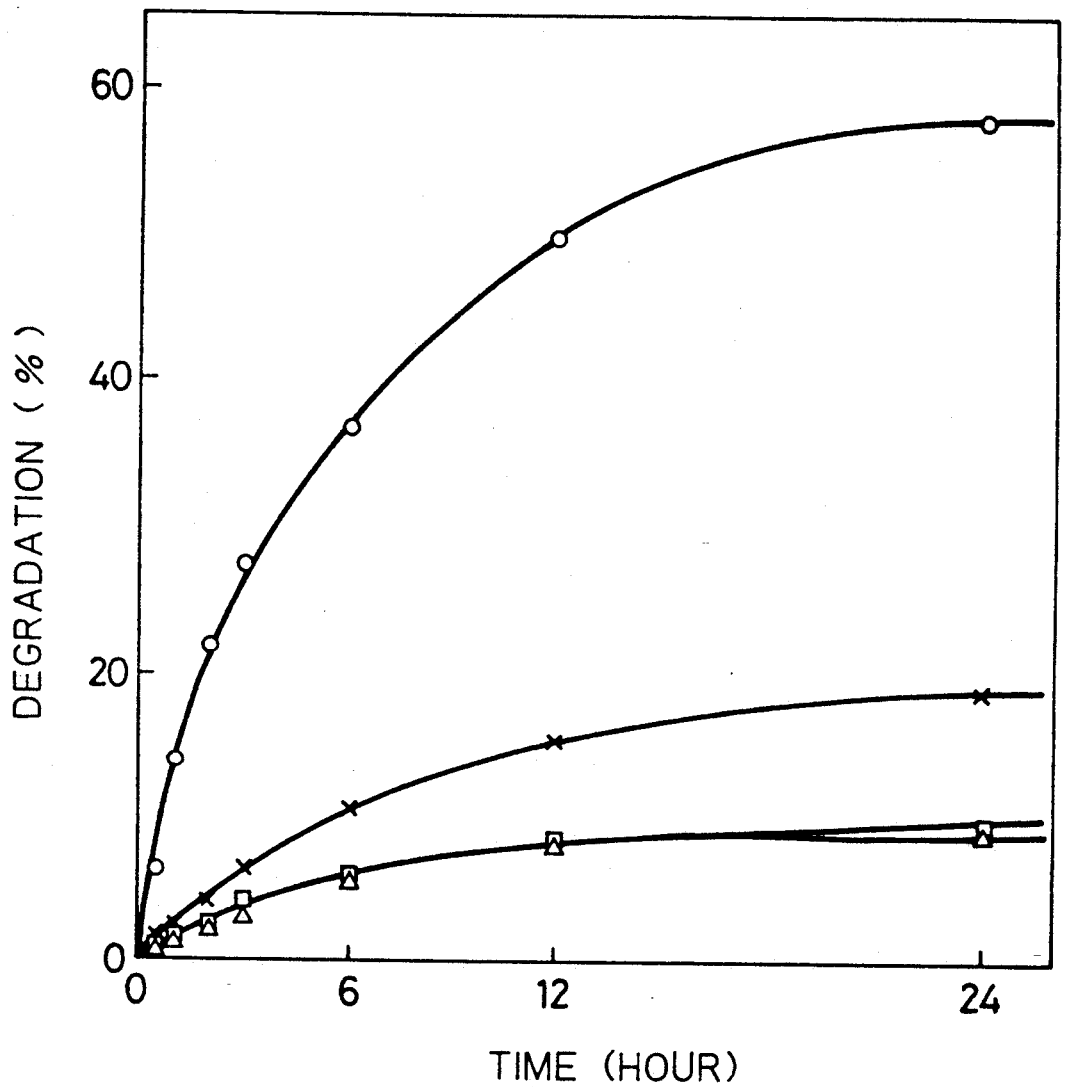
FIG. 1 shows the comparison of insoluble glucan-degrading percentage between the endodextranase from *Arthrobacter globiformis* W31 and those derived from other fungi.

The present inventors had already searched for novel dextranase-producing strains and found that a gram-positive soil bacterium Arthrobacter qlobiformis W31 [NRRL B-4428 (NRRL: Northern Regional Research Laboratory, Peoria, Ill., U.S.A.)] and its mutants can produce novel endodextranase. They have provided therefore a method for manufacturing industrially utilizable endodextranase by using the strain or mutants thereof (Japanese Patent Application Nos. 52661 and 52662/1988). Now, the inventors have surprisingly found that the endodextranases I and II from this gram-positive bacterium *Arthrobacter globiformis* W31 (NRRL B-4428) can degrade insoluble glucan produced by *Streptococcus mutans* 3–6 times more effectively than those of other origins even when used alone. The inventors have also found that the combined use of the present endodextranase with α-amylase from various microorganisms leads to a marked synergistic effect on the degradation of the aforementioned insoluble glucan.

Thus, the present invention relates to a dental plaque-degrading composition containing endodextranase which is produced by a microorganism belonging to the genus Arthrobacter, and also relates to a dental plaque-degrading composition containing α-amylase in addition to the endodextranase.

The present invention will be described in detail hereinafter.

Preferable endodextranase which may be mentioned are, for example, endodextranases I and II derived from gram-positive soil bacterium *Arthrobacter globiformis* W31 (NRRL B-4428) as disclosed in the above mentioned applications (Japanese Patent Application Nos. 52661/1988 and 52662/1988). In addition to the above strain, the mutants thereof and other strains belonging to the genus Arthrobacter and the mutants thereof may also be used so far as they are capable of producing endodextranase.

The properties of the above described endodextranases I and II are as follows:

Endodextranase I:

(1) Action:

Acts upon dextran to produce mainly isomaltotriose and isomaltotetraose.

(2) Substrate Specificity:

Hydrolyzes mainly bacterial dextran.

(3) Optimal pH and Stable pH Range:

Acts within the pH range of 4.0 to 7.5 and has optimal pH around 6.0 [measured using 0.25% dextran (T2000 manufactured by Pharmacia Fine Chemicals, Inc.); reaction time, 6 minutes; reaction temperature, 30° C.]

Stable within the pH range of 5.0 to 7.5 (determined by measuring residual activities, after leaving in 50 mM $\beta,\beta'$-dimethyl glutarate buffer containing 5 mM $CaCl_2$ at 4° C. for 24 hours).

(4) Active Temperature Range and Optimal Temperature:

Acts at temperatures ranging from approx. 20 to 55° C., and the optimal temperature is around 45° C. (in 0.25% dextran, 6 minutes, at pH 6.0).

(5) Thermostability:

After heating to various temperatures at pH 6.0 for 10 minutes, the residual activities were determined. It was found that the residual activity was 100% when heated to below 45° C., approx. 60% when heated at 50° C. and substantially inactivated when heated at 60° C.

(6) Molecular Weight:

Approximately 107,000 as measured by SDS-polyacrylamide gel electrophoresis (SDS-PAGE).

(7) Isoelectric Point (pI):

4.29 as measured in an isoelectrofocusing apparatus (110 ml column) [manufactured by LKB Co., Ltd.].

(8) Inhibition, Activation and Stabilization:

Inhibited by the presence of 5 mM heavy metal ion such as mercury, copper or the like; also by the same concentration of $KMnO_4$, N-bromosuccinimide, etc.

Activated by 5 mM calcium ion.

Endodextranase II:

(1) Action:

Acts on dextran to produce mainly isomaltotriose and isomaltotetraose.

(2) Substrate Specificity:

Hydrolyzes mainly bacterial dextran.

(3) Optimal pH and Stable pH Range:

Acts within the pH range of 4.5 to 7.0 and has optimal pH around 6.0 [measured using 0.25% dextran (T2000 manufactured by Pharmacia Fine Chemicals, Inc.); reaction time, 6 minutes; reaction temperature, 30° C.].

Stable within the pH range of 5.0 to 7.5 (determined by measuring the residual activities after leaving in 50 mM $\beta,\beta'$-dimethyl glutarate buffer containing 5 mM $CaCl_2$ at 4° C. for 24 hours).

(4) Active Temperature Range and Optimal Temperature:

Acts at temperatures ranging from approx. 20 to 55° C., and the optimal temperature is around 40° C. (in 0.25% dextran, 6 minutes, at pH 6.0).

(5) Thermostability:

After heating to various temperatures at pH 6.0 for 10 minutes, the residual activities were determined. It was found that the residual activity was 100% when heated to below 40° C., approx. 60% when heated at 45° C. and substantially inactivated when heated at 55° C.

(6) Molecular Weight:

Approximately 70,000 as measured by SDS-polyacrylamide gel electrophoresis (SDS-PAGE).

(7) Isoelectric Point (pI):

4.51 as measured in an isoelectrofocusing apparatus (110 ml column [manufactured by LKB Co., Ltd.].

(8) Inhibition, Activation and Stabilization:

Inhibited by the presence of 5 mM heavy metal ion such as mercury, copper or the like; also by the same concentration of $KMnO_4$, N-bromosuccinimide, etc.

Activated by 5 mM calcium ion.

These endodextranases can be obtained according to the method described in the afore-mentioned applications (Japanese Patent Application Nos. 52661/1988 and 52662/1988). For example, as follows:

Endodextranases I and II are produced by inducing *Arthrobacter globiformis* W31 [NRRL B-4428 (NRRL: Northern Regional Research Laboratory, Peoria, Ill., U.S.A.)] with dextran as a sole carbon source.

As nitrogen source, organic nitrogen-containing substances such as various amino acids, malt extracts, peptone, meat extracts, urea, etc. and inorganic nitrogen compounds such as ammonium chloride, ammonium sulfate, ammonium nitrate, etc., may be used alone or in combinations thereof.

Besides, it is preferred timely to add minerals, vitamins, etc. The addition of asparagine to a culture medium can increase the productivity of endodextranases I and II.

Suitable culture temperature is 20 to 35° C., preferably 28 to 30° C. Suitable culture pH is 5.5 to 8.5, preferably 6.0 to 6.5. The culture period is 2 to 3 days. Although the present strain can be cultured either by liquid culture or solid culture, it is preferably cultured by liquid culture under aerobic condition.

After the completion of the culture, endodextranases I and II can be recovered by known methods. For example, cells in the culture are removed by centrifugation to obtain the cell-free supernatant. Then, the supernatant is salted out with 90% saturated ammonium sulfate. After dialyzing the precipitate obtained against 20 mM acetate buffer (pH 6.0) containing 5 mM calcium ion, the dialysate is loaded onto a DEAE-Sepharose column. Active fractions eluted with 0.2M sodium chloride were subjected to gel-filtration through a Bio-Gel P-150 column. Active fractions eluted early are further loaded onto a DEAE-Sepharose column, whereby purified endodextranase I can be obtained. Furthermore, active fractions eluted late in the aforementioned gel-filtration using Bio-Gel P-150 can also be loaded onto a DEAE-Sepharose column to give purified endodextranase II.

Endodextranase used in the present invention is not necessarily purified. It may be used in the form of crude enzyme solution obtained by removing cells from the culture.

Any α-amylase can be used in the recent dental plaque-degrading composition together with the endodextranase, for example, those derived from microorganisms belonging to the genera Bacillus, Aerobacter, Asperqillus, Streptomyces, Pseudomonas, etc., those derived from higher plants such as barley malt, etc.; salivary α-amylase; etc.

Specific examples of the dental plaque-degrading compositions according to the present invention include various types of dentifrices, denture detergents, solid oral refrigerants such as a troche and the like, liquid oral refrigerants such as a mouth wash and the like, oral compositions such as a chewing gum and the like, various candies, etc.

Hereinafter, the present invention will be described, referring to specific Examples.

Insoluble glucan used in the Examples were prepared in the following manner. A liquid medium (pH 7.0, 300 ml×10) containing 10% sucrose, 0.05% $MgSO_4 \cdot 7H_2O$, 0.2% $K_2HPO_4$ and 1% polypeptone was inoculated with cariogenic streptooooocus (Streptococcus mutans IFO 13955), followed by stationary culture at 37° C. for 4 days. The resultant culture was filtered through a filter paper (No. 2) [Advantic Co., Ltd.] to remove insolubles. The insolubles remaining on the filter paper were washed thoroughly with distilled water. A suspension of the residue in approx. 200 ml of distilled water was concentrated using a rotary evaporator (60° C.) and then freeze-dried. After these operations, approx. 4.8 g of freeze-dried preparation of insoluble glucan was obtained from 3 l of the culture.

The enzymatic activities of the dextranase and amylase were calculated by reacting a solution consisting of 0.5 ml of 1.0% dextran T2000 solution or 0.3% soluble starch solution and 1.0 ml of acetate buffer (pH 6.0) containing 5 mM $Ca^{2+}$ with 0.5 ml of enzyme solution at 30° C. for a given period of times. The amount of reducing sugar formed per 1.0 ml of the reaction mixture was determined according to the Somogyi-Nelson method. 1 unit of the enzyme activity is defined as the value capable of producing reducing sugar corresponding to 1 μmol of glucose in 1 minute under these conditions.

EXAMPLE 1

Streptocuccus mutans IFO 13955 was cultured without shaking in a liquid medium (pH 7.0) containing 10% sucrose, 0.05% $MgSO_4 \cdot 7H_2O$, 0.2% $K_2HPO_4$ and 1% polypeptone at 37° C. for 14 days. As a result of inserting stainless wire in the medium from the beginning of the culture, a large amount of artificial plaque was formed and adhered on the stainless wire. Into large test tubes (18×180 mm) was added 15 ml each of respective solutions containing 15 unit of crude endodextranase or highly purified endodextranase I or II, all prepared from Arthrobacter globiformis W31 (NRRL B-4428) according to the afore-mentioned method (Japanese Patent Application Nos. 52661/1988 and 52662/1988). Then, the artificial plaque-adhered stainless wire formed as above was immersed in each of the above solution at pH 6.0 at 30° C. for 20, 40 and 60 minutes. In all cases, the artificial plaque was degraded, solubilized and then completely dropped off from the stainless wire after 40 minutes.

As mentioned above, it has been confirmed that the endodextranase from Arthrobacter globiformis W31 (NRRL B-4428) is capable of strongly degrading and solubilizing insoluble glucan which is the principal constituent of dental plaque.

EXAMPLE 2

100 μl each of solutions respectively containing 0.27 unit of purified endodextranase I or II from Arthrobacter globiformis W31 (NRRL B-4428) was added to 2.4 ml of 20 mM acetate buffer (pH 6.0, +5 mM $Ca^{2+}$ containing 0.2% of the aforementiohed insoluble glucan and allowed to react at 37° C. Furthermore, solutions of commercially available dextranase preparations originated from Chaetomium gracile, Penicillium lilacinum, Penicillium funiculosum, (these solutions were so prepared as to contain 0.27 unit each of dextranase) were allowed to react with insoluble glucan under the same reaction conditions as above, as controls. Reducing sugar formed with the elapse of time was determined according to the Somogyi-Nelson method. The amount of sugar component initially present in the insoluble glucan was also determined according to the phenol-sulfuric acid method, and the degradation % of insoluble glucan was calculated.

From the results obtained (see FIG. 1), it is clear that Arthrobacter globiformis W31 (NRRL B-4428) endodextranase showed about 3 times more degradation % than that from Chaetomium, and about 6 times more than that from Penicillium.

EXAMPLE 3

Figure 2:
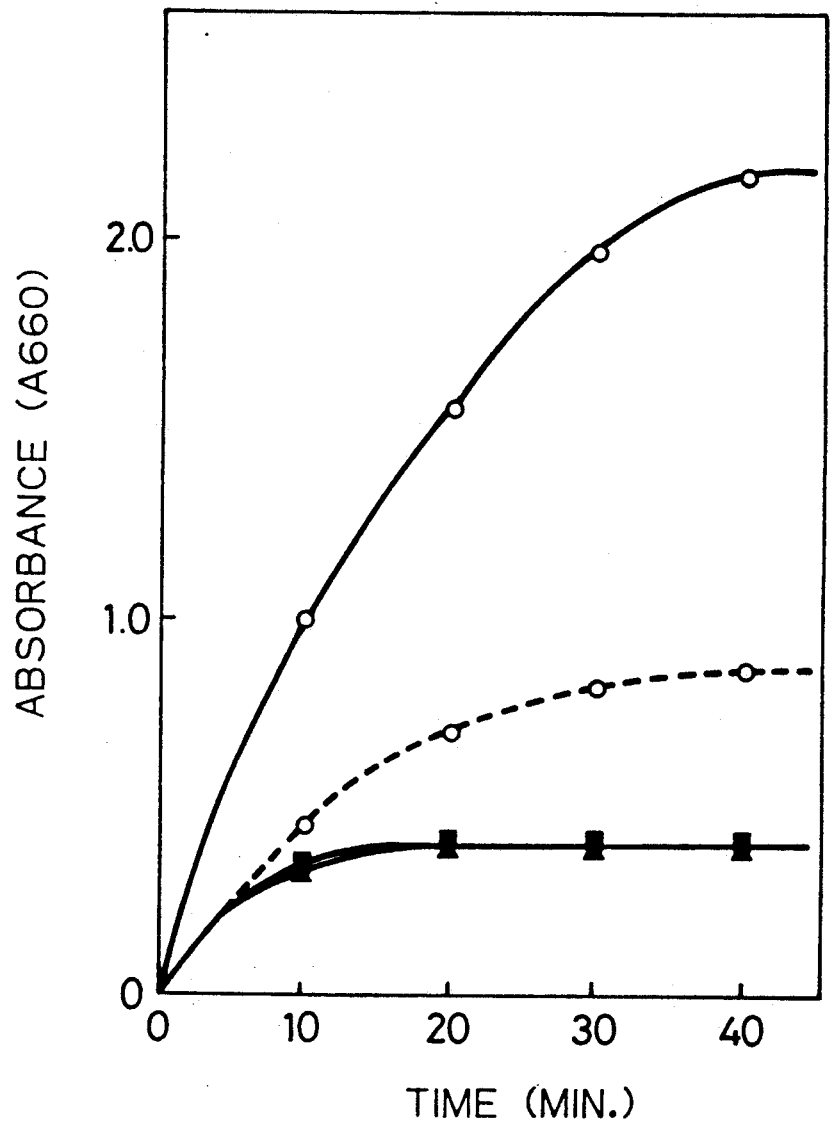
FIG. 2 shows the comparison of insoluble glucan-degrading activity between the endodextranase from *Arthrobacter globiformis* W31 and various α-amylases of different origins.

100 μl each of solutions respectively containing 0.3 or 1.0 unit each of purified endodextranase I or II originated from Arthrobacter globiformis W31 (NRRL B-4428) was added to 2.4 ml of 20 mM acetate buffer (pH 6.0, +5 mM $Ca^{2+}$) containing 0.2% of the aforementioned insoluble glucan and allowed to react at 37° C. Separately, 1.0 unit each of commercially available α-amylase preparations, namely barley malt α-amylase (manufactured by SIGMA, Inc.) crystalline α-amylase from Bacillus sp. (manufactured by SIGMA, Inc.), and crystalline α-amylase from Bacillus licheniformis was added to insoluble glucan under the same reaction conditions as above. The amount of reducing sugar formed with the elapse of time was determined according to the Somogyi-Nelson method. The respective activities of the enzymes in degrading insoluble glucan were shown by the absorbance at 660 nm (see FIG. 2).

From the results obtained, it is clear that all the tested α-amylase contributed to the initial degradation of insoluble glucan.

EXAMPLE 4

Each 100 μl of solutions respectively containing 0.3 or 1.0 unit of purified endodextranase I or II from *Arthrobacter globiformis* W31 (NRRL B-4428), or containing 0.3 unit of the purified endodextranase in combination with 0.7 unit of barley malt α-amylase (manufactured by SIGMA, Inc.), Bacillus sp. crystalline α-amylase (manufactured by SIGMA, Inc.), human salivary α-amylase (manufactured by SIGMA, Inc.), or *Bacillus licheniformis* crystalline α-amylase was added to 2.4 ml of 20 mM acetate buffer (pH 6.0, +5 mM $Ca^{2+}$) containing 0.2% of the aforementioned insoluble glucan, and the mixture thus obtained was allowed to react at 37° C. The amount of reducing sugar formed with the elapse of time was determined according to the Somogyi-Nelson method, and insoluble glucan-degrading activity was shown by the absorbance at 660 nm (see FIG. 3).

From the results obtained, it is clear that the combined use of the enzyme from Arthrobacter qlobiformis W31 (NRRL B-4428) with a proper amount of α-amylase of various microbial origins gave a marked synergistic effect upon the initial degradation of insoluble glucan and therefore permitted the reduction in the amount of endodextranase to be used.

EXAMPLE 5

100 μl each of solutions respectively containing purified endodextranase I or II (0.3 unit) from *Arthrobacter globiformis* W31 (NRRL B-4428), or containing *Bacillus licheniformis* α-amylase (1.0 unit), or containing purified endodextranase (0.1 unit) in combination with *Bacillus licheniformis* α-amylase (0.9 unit), or containing purified endodextranase (0.2 unit), in combination with *Bacillus licheniformis* α-amylase (0.8 unit), or containing purified endodextranase (0.3 unit) in combination with *Bacillus licheniformis* α-amylase (0.7 unit) was added to 2.4 ml of 20 mM acetate buffer (pH 6.0, +5 mM $Ca^{2+}$) containing 0.2% of the aforementioned insoluble glucan and allowed to react at 37° C. The amount of reducing sugar formed with the elapse of time was determined according to the Somogyi-Nelson method. The enzymatic activity in degrading insoluble-glucan was shown by the absorbance at 660 nm (see FIG. 4).

From the results obtained, it is clear that the combined use of purified endodextranase with α-amylase gave a marked synergistic effect upon the initial degradation of insoluble glucan and allowed for the reduction in the amount of endodextranase to be used.

What is claimed is:

1. A dental plaque-degrading composition in the form of a dentifrice, a denture detergent, a troche, a mouth wash, a chewing gum or a candy comprising endodextranase produced by *Anthrobacter globiformis* W31 (NRRL B-4428) in an amount effective to degrade dental plaque.

2. A dental plaque-degrading composition in the form ofa dentifrice, a denture detergent, a troche, a mouth wash, a chewing gum or a candy comprising endodextranase produced by *Anthrobacter globiformis* W31 (NRRL B-4428) and αamylase, in amounts effective to degrade dental plaque.

3. The dental plaque-degrading composition of claim 1 wherein the effective amount of endodextranase is at least 1 unit.

4. The dental plaque-degrading composition of claim 2 wherein the effective amounts of endodextranase and α-amylase are at least 0.3 unit and at least 0.7 unit, respectively.

5. In the process of enzymatically degrading, solubilizing and/or removing adhered insoluble glucan in dental plaque, with endodextranase, the improvement, which permits a 3-6 fold reduction in the effective amount of endodextranase to be used, as compared to enzymatically equivalent amounts of an endodextranase derived from microorganisms belonging to the genera Chaetonium or Penicillium, consists essentially of contacting said adhered dental plaque with a composition comprising an amount, effective to degrade dental plaque, of endodextranase produced by *Arthrobacter globiformis* W31 (NRRL B-4428).

6. The process of claim 5 wherein adhered dental plaque is contacted with a composition comprising amounts, effective to degrade dental plaque, of endodextranase produced by *Arthrobacter globiformis* W31 (NRRL B-4428) and α-amylase.

7. The process of claim 5 wherein adhered dental plaque is contacted with a composition comprising at least 0.3 unit and 0.7 unit, respectively, of endodextranase produced by *Arthrobacter globiformis* W31 (NRRL B-4428) and α-amylase.

* * * * *

UNITED STATES PATENT AND TRADEMARK OFFICE
CERTIFICATE OF CORRECTION

PATENT NO.  : 5,085,851
DATED       : February 4, 1992
INVENTOR(S) : GENTARO OKADA, ET AL.

It is certified that error appears in the above-identified patent and that said Letters Patent is hereby corrected as shown below:

Title Page, List of Inventors, change "Kawamura, Kounan, all of Japan"

to --Yoshiya Kawamura, Kounan, all of Japan--.

Signed and Sealed this

Eighth Day of June, 1993

Attest:

MICHAEL K. KIRK

Attesting Officer  Acting Commissioner of Patents and Trademarks